United States Patent
Rodd et al.

(10) Patent No.: US 9,615,782 B2
(45) Date of Patent: Apr. 11, 2017

(54) BLOOD FLASH NEEDLE

(75) Inventors: Aaron Leonard Rodd, Burleigh Waters (AU); Ross Joseph Cali, Eight Mile Plains (AU)

(73) Assignee: MEDIGARD LIMITED, Robina (AU)

( * ) Notice: Subject to any disclaimer, the term of this patent is extended or adjusted under 35 U.S.C. 154(b) by 0 days.

(21) Appl. No.: 13/503,571

(22) PCT Filed: Oct. 11, 2010

(86) PCT No.: PCT/AU2010/001334
§ 371 (c)(1),
(2), (4) Date: May 22, 2012

(87) PCT Pub. No.: WO2011/047413
PCT Pub. Date: Apr. 28, 2011

(65) Prior Publication Data
US 2012/0232424 A1    Sep. 13, 2012

(30) Foreign Application Priority Data
Oct. 22, 2009   (AU) ................................ 2009905146

(51) Int. Cl.
*A61B 5/00* (2006.01)
*A61B 5/15* (2006.01)
(Continued)

(52) U.S. Cl.
CPC .... *A61B 5/150488* (2013.01); *A61B 5/15003* (2013.01); *A61B 5/1535* (2013.01); *A61B 5/1545* (2013.01); *A61B 5/150259* (2013.01); *A61B 5/150389* (2013.01); *A61B 5/150511* (2013.01); *A61B 5/150519* (2013.01); *A61B 5/150572* (2013.01); *A61B 5/150587* (2013.01);
(Continued)

(58) Field of Classification Search
USPC .................................................. 600/573, 576
See application file for complete search history.

(56) References Cited

U.S. PATENT DOCUMENTS 7,063,673 B2 *  6/2006  Marsden ....................... 600/576
7,396,343 B2 *  7/2008  Brown .......................... 604/122
(Continued)

FOREIGN PATENT DOCUMENTS

CN          2059347 U       7/1990
EP          0139872 A1      5/1985
(Continued)

OTHER PUBLICATIONS

International Search Report; International Application No. PCT/AU2010/001334; International Application Filing Date: Oct. 11, 2010; Mail date Nov. 12, 2010.
(Continued)

*Primary Examiner* — Daniel Cerioni
(74) *Attorney, Agent, or Firm* — Cantor Colburn LLP

(57) ABSTRACT

A device for drawing fluid from a lumen comprising a body, a first needle portion extending from a forward portion of the body and a second needle portion extending from a rear portion of the body, wherein the body includes an observation portion adapted to allow visual observation of the fluid, and wherein the observation portion is provided with enhancement means adapted to enhance the visibility of the fluid in the observation portion.

13 Claims, 4 Drawing Sheets

(51) Int. Cl.
  *A61B 5/153* (2006.01)
  *A61B 5/154* (2006.01)
  *A61B 5/155* (2006.01)

(52) U.S. Cl.
  CPC .. *A61B 5/150702* (2013.01); *A61B 5/150717* (2013.01); *A61B 5/150732* (2013.01); *A61B 5/155* (2013.01)

(56) References Cited

U.S. PATENT DOCUMENTS

| | | | |
|---|---|---|---|
| 7,530,967 B2* | 5/2009 | Brown | 604/122 |
| 2002/0049391 A1* | 4/2002 | Kuracina et al. | 600/576 |
| 2003/0105414 A1* | 6/2003 | Leong | 600/576 |
| 2004/0210197 A1* | 10/2004 | Conway | 604/198 |
| 2005/0245870 A1 | 11/2005 | Brown | |
| 2005/0283093 A1* | 12/2005 | Conway et al. | 600/576 |
| 2006/0116660 A1 | 6/2006 | Cawley | |
| 2007/0265549 A1* | 11/2007 | Channer et al. | 600/576 |
| 2008/0177202 A1* | 7/2008 | Brown | 600/579 |
| 2008/0194986 A1* | 8/2008 | Conway et al. | 600/579 |
| 2009/0043225 A1* | 2/2009 | Conway et al. | 600/579 |
| 2009/0088698 A1 | 4/2009 | Steube | |
| 2009/0204026 A1* | 8/2009 | Crawford et al. | 600/576 |
| 2009/0227896 A1* | 9/2009 | Alvin Tan et al. | 600/576 |
| 2009/0227953 A1 | 9/2009 | Tan et al. | |
| 2009/0259145 A1* | 10/2009 | Bartfeld | A61B 5/1405 600/576 |

FOREIGN PATENT DOCUMENTS

| | | |
|---|---|---|
| EP | 1232766 A2 | 8/2002 |
| JP | 11169359 A | 6/1999 |
| JP | 2002248170 A | 9/2002 |
| JP | 200982714 A | 4/2009 |
| WO | 2004062499 A1 | 7/2004 |
| WO | 2005070292 A1 | 8/2005 |
| WO | 2008042293 A2 | 4/2008 |

OTHER PUBLICATIONS

Written Opinion; International Application No. PCT/AU2010/001334; International Application Filing Date: Oct. 11, 2010; Mail date Nov. 12, 2010.

International Preliminary Repor on Patentability; International Application No. PCT/AU20101001334; International Application Filing Date: Oct. 11, 2010; Mail date Nov. 12, 2010.

European Search Report for corresponding application EP10824395; Report Date Mar. 22, 2013.

\* cited by examiner

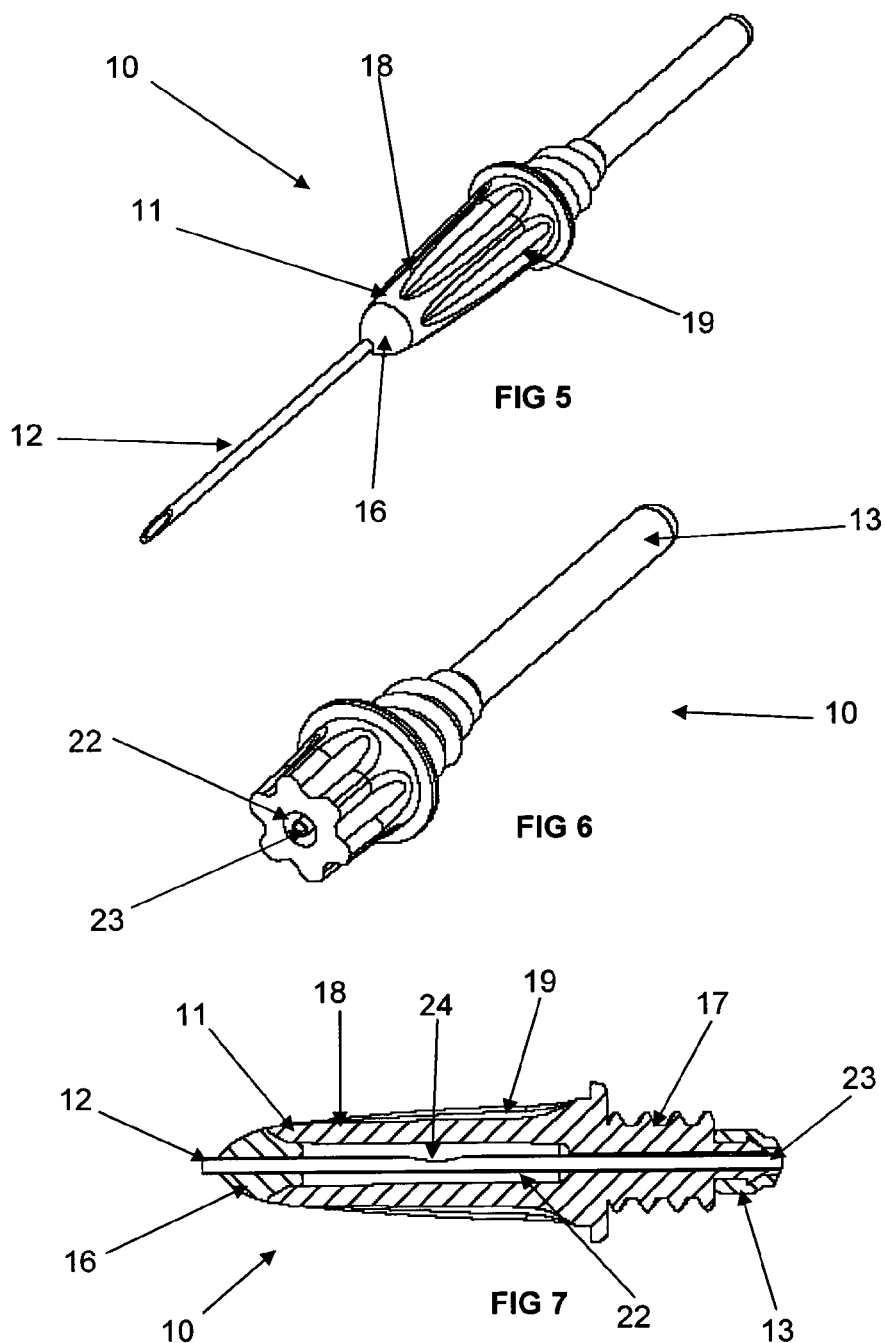

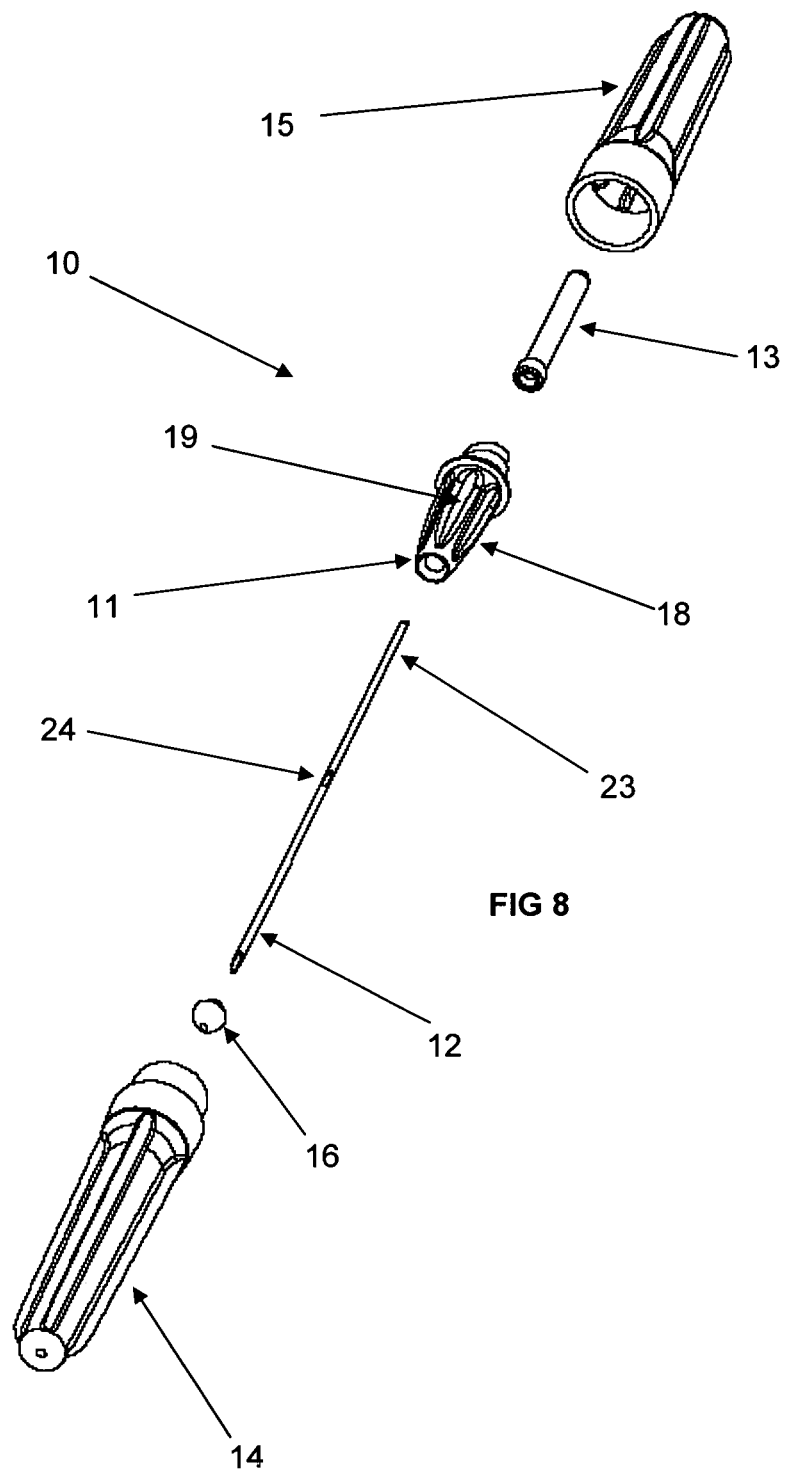

BLOOD FLASH NEEDLE

FIELD OF THE INVENTION

The present invention relates to a device for drawing fluid from a lumen. In particular, the present invention relates to a device for drawing blood from a blood vessel.

BACKGROUND ART

Intravenous blood collection devices have long been used to draw bodily fluids from patients. Typically, collecting a bodily fluid, such as blood, involves inserting a needle into a vessel or lumen from which the fluid is to be drawn and then collecting the fluid as it flows through the needle.

However, in situations in which the vessel or lumen is small or not visible, it may be difficult to locate the tip of the needle within the vessel. Not only does this have the potential to undermine the integrity of the sample, but a failure to correctly locate the tip of the needle could also cause injury to the patient should the needle come into contact with tissue or organs. As a result, it is desirable to provide a mechanism that allows for confirmation of the correct positioning of the tip of the needle.

In the past, some intravenous blood collection devices have been provided with transparent windows that allow a user to observe a "flash" of blood that confirms that the needle tip is correctly positioned. However, the flash may be small or obscured, meaning that it may be difficult to detect.

Thus, there would be an advantage if it were possible to provide a blood collection device that provided a user with a clear visual indication of the correct positioning of a needle.

It will be clearly understood that, if a prior art publication is referred to herein, this reference does not constitute an admission that the publication forms part of the common general knowledge in the art in Australia or in any other country.

Throughout this specification, the term "comprising" and its grammatical equivalents shall be taken to have an inclusive meaning unless the context of use indicates otherwise.

OBJECT OF THE INVENTION

It is an object of the present invention to provide a device for drawing fluid from a lumen which may overcome at least some of the abovementioned disadvantages, or provide a useful or commercial choice.

In one aspect, the invention resides broadly in a device for drawing fluid from a lumen comprising a body, a first needle portion extending from a forward portion of the body and a second needle portion extending from a rear portion of the body, wherein the body includes an observation portion adapted to allow visual observation of the fluid, and wherein the observation portion is provided with enhancement means adapted to enhance the visibility of the fluid in the observation portion.

In an alternative aspect, the invention resides in a device for drawing fluid from a lumen comprising a body, a first needle portion extending from a forward portion of the body and a second needle portion extending from a rear portion of the body, wherein the body includes an observation portion adapted to allow visual observation of the fluid, and wherein the observation portion is configured to enhance the visibility of the fluid in the observation portion.

The first and second needle portions may be of any suitable size, shape or configuration. Preferably, however, the first and second needle portions are substantially tubular so that a fluid (for instance, blood) may flow through the first and second needle portions.

In a preferred embodiment of the invention, the first needle portion may be adapted to be inserted into a patient's body. For instance, the first needle portion may be adapted to pierce or puncture the patient's skin and enter a lumen (such as a blood vessel) from which fluid may be drawn. Thus, in a preferred embodiment of the present invention, the first needle portion is adapted to function as a puncture needle.

Preferably, the second needle portion is adapted to be brought into communication with a medical device. For instance, the second needle portion may be adapted to be brought into contact with a fluid collection vessel (such as a vial, test tube, flask, bag or the like), a flexible tube, a syringe or the like. In some embodiments of the invention, the medical device may be provided with a seal, meaning that the second needle portion may be required to pierce of puncture the seal (such as a plug, bung, membrane or the like) in order to be brought into communication with the medical device. Thus, in a preferred embodiment, the second needle portion is adapted to function as a puncture needle.

In a preferred embodiment, the second needle portion may be provided with covering means adapted to prevent leakage of fluid from the second needle portion before the second needle portion is brought into contact with a medical device. Any suitable covering means may be used, although in a preferred embodiment of the invention, the covering means may comprise a flexible sheath adapted to prevent any fluid exiting the second needle portion from leaking out of the device. It is envisaged that, when the second needle portion is brought into communication with a medical device, the second needle portion will puncture the covering means, thereby allowing fluid to flow from the second needle portion into the medical device.

In some embodiments, the first needle portion may form a part of a first needle, while the second needle portion may form a part of a second needle, the first and second needles being spaced apart from one another within the body of the device. However, in a preferred embodiment of the invention, the first and second needle portions form part of a single needle. In this embodiment, it is envisaged that the first and second needle portions form opposing ends of a single needle.

In embodiments of the invention in which the first and second needle portions form part of a single needle, it is preferred that the needle extends entirely through the body such that the first needle portion extends from a forward portion of the body while the second needle portion extends from a rear portion of the body. Thus, it is envisaged that the body may comprise a passageway or bore therein through which the needle may be passed.

The passageway may be of any suitable dimensions, however in a preferred embodiment of the invention, the passageway has a diameter along at least a portion of its length that is large enough to retain the needle in the passageway in a frictional engagement. Typically, this frictional engagement may occur at or toward the forward of rearward end of the body.

In a preferred embodiment of the invention, the passageway may include a chamber portion along a portion of its length. Preferably, the chamber portion is of a greater diameter than the remainder of the passageway such that a gap is formed between the needle and the inner wall of the chamber portion. In this embodiment of the invention, it is preferred that the needle is provided with one or more apertures that, when the device is assembled, align with the chamber portion. In use, it is envisaged that a portion of the fluid flowing through the needle will enter the chamber portion through the one or more apertures in the needle.

The chamber portion may be of any suitable size or configuration. For instance, the chamber portion may extend entirely about the circumference of the needle, thereby comprising an annular chamber surrounding the needle. Alternatively, the chamber portion may extend only partially around the circumference of the needle.

Preferably, the volume of the chamber portion is relatively small. For instance, it is preferred that the volume of the chamber is smaller than the volume of the needle over which the chamber lies such that only a small amount of fluid is required to be diverted out of the needle and into the chamber before the chamber is filled. Thus, the chamber may be or form a part of the enhancement means that enables a user to observe the fluid in the chamber portion, rather than a large volume of fluid being required to enable the user to view the fluid. If the chamber is annular, another advantage of the invention will be that the fact that the fluid is present will be ascertainable from any direction when viewing the device. A smaller volume of fluid can be used in the annular chamber than would be used to fill a cylindrical chamber and the annual chamber will typically have a larger surface area than a cylindrical chamber of the same volume.

In a preferred embodiment, the observation portion of the body is fabricated from a transparent or semi-transparent material (such as glass or plastic). Preferably, the observation portion is substantially aligned with the chamber portion of the passageway such that fluid entering the chamber portion may be observed through the observation portion of the body. The observation portion may comprise a portion of the outer surface of the body. Alternatively, the entire body may be fabricated from a transparent or semi-transparent material so that the flow of fluid may be observed from any angle. This is particularly the case if the chamber portion extends entirely about the circumference of the needle.

As previously stated, the observation portion is provided with enhancement means to enhance the visibility of the fluid in the observation portion. By this it is meant that the user's ability to see the fluid is enhanced by the enhancement means.

The enhancement means may be of any suitable form. However, in a preferred embodiment of the invention the enhancement means comprise one or more recesses or shaped portions in the body. The recesses may be of any suitable size, shape or configuration. For instance, the one or more recesses may be in the form of one or more dimples in the surface of the body. Alternatively, the one or more recesses may be in the form of channels or grooves extending in one or more directions along the surface of the body.

In a preferred embodiment, the one or more recesses are shaped so as to refract, multiply and/or enhance the image of the fluid in the chamber portion to make the fluid easier for a user to see. Thus, it is preferred that the one or more recesses are substantially concave in order to improve the refraction, multiplication and/or enhancement of the image of the fluid in the chamber portion.

It is further provided that the enhancement means may be a particular colour as some colours or tints will make some fluids more visible to the naked eye of an operator. It is also possible that the enhancement means may contain a material to react with the fluid to make the fluid more easily visible to the naked eye of an operator. The enhancement means may therefore be a physical enhancement means or a chemical enhancement means.

If the frictional engagement between the needle and the passageway is not sufficient to retain the needle within the body, retaining means may be used to retain the needle in place. Preferably, the retaining means are adapted to seal one or more ends of the body (in order to prevent leakage of fluid) and/or to retain the needle in place. For instance, one or both of the front and rear portions of the body may be provided with retaining means such as retaining caps or retaining plugs. Alternatively, the retaining means may be in the form of a settable or hardenable material, such as an adhesive or a thermosetting plastic, applied to one or more ends of the body. In this embodiment, the needle is retained in place by the set or hardened material. In embodiments of the invention in which retaining caps or retaining plugs are present, one or both of the retaining caps or retaining plugs and the body may be provided with engagement means adapted to improve the engagement between the retaining caps or retaining plugs and the body. Alternatively, the retaining caps or retaining plugs may be retained within the body using adhesives or the like.

In some embodiments of the invention, the rear portion of the body (or, if present, the retaining device located at the rear of the body) may be provided with connection means adapted to allow the device to be connected to a suitable medical device. The connection means may be of any suitable form. For instance, the connection means may be one or more projections, clips, fasteners or the like. Alternatively, the connection means may comprise a screw-threaded portion adapted for connection to a complementary screw-threaded portion in a medical device. The connection means will typically be provided on a rear portion of the body adjacent the second needle portion.

In a preferred embodiment of the invention, one or both of the first and second needle portions may be provided with needle caps during transportation and storage. In this way, damage to the needle portions may be prevented, and the likelihood of a user accidentally injuring themselves on the needle portions is reduced.

In another aspect, the invention resides broadly in a device for drawing blood from a lumen, comprising a body, a first needle portion extending from a forward portion of the body and a second needle portion extending from a rear portion of the body, wherein the body includes a transparent observation portion adapted to allow visual observation of the blood, and wherein the observation portion is provided with one or more recesses adapted to enhance the visibility of the blood in the observation portion.

BRIEF DESCRIPTION OF THE DRAWINGS

An embodiment of the invention will be described with reference to the following drawings in which:

FIG. 5 illustrates a perspective view of a device for drawing fluid from a lumen according to an embodiment of the present invention;

FIG. 6 illustrates a sectional perspective view of a device for drawing fluid from a lumen according to an embodiment of the present invention;

FIG. 7 illustrates a cross-sectional view of a device for drawing fluid from a lumen according to an embodiment of the present invention;

FIG. 8 illustrates an exploded perspective view of a device for drawing fluid from a lumen according to an embodiment of the present invention.

DETAILED DESCRIPTION OF THE DRAWINGS

Figure 1:
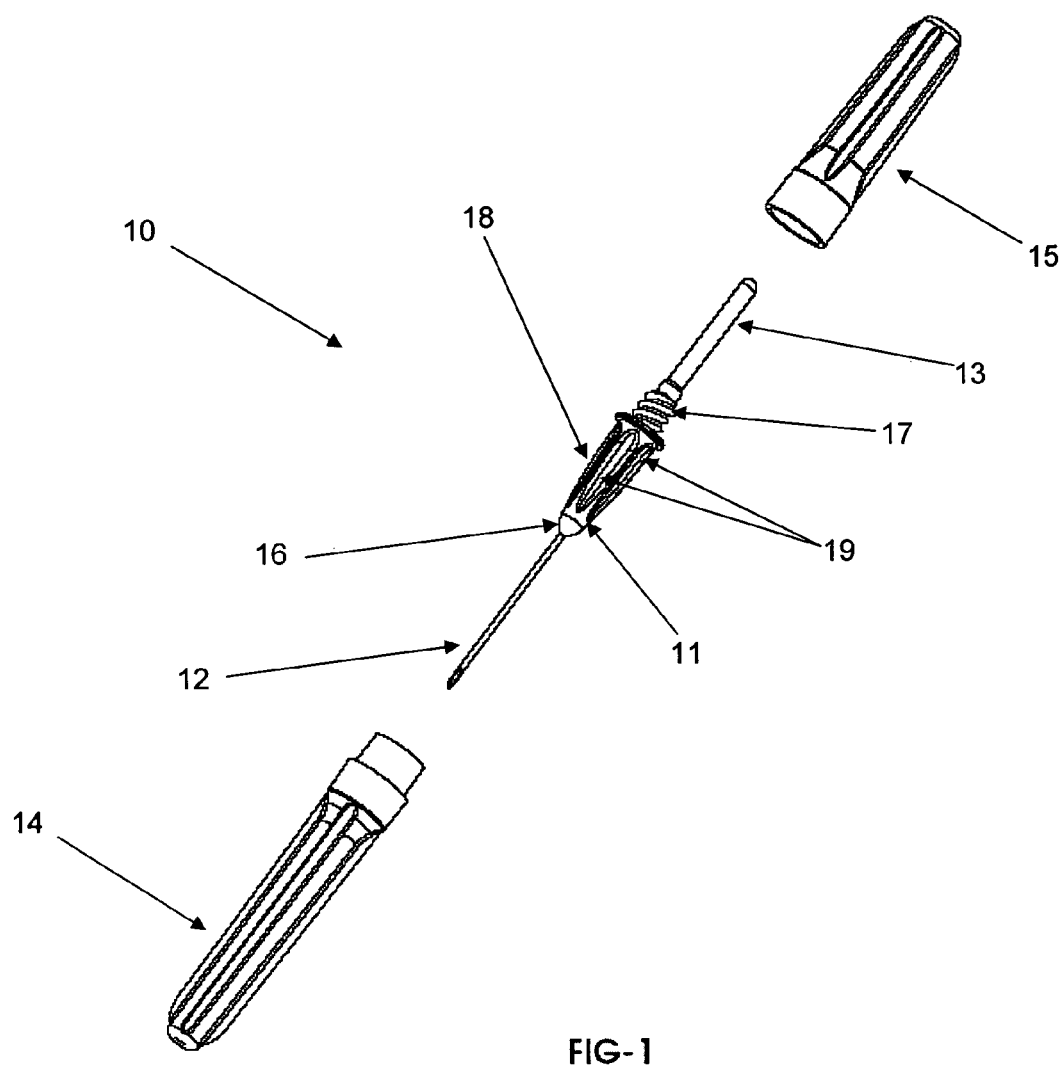
FIG. 1 illustrates a perspective view of a device for drawing fluid from a lumen according to an embodiment of the present invention.

It will be appreciated that the drawings have been provided for the purposes of illustrating preferred embodiments of the present invention and that the invention should not be considered to be limited solely to the features as shown in the drawings.

In FIG. 1 there is shown a perspective view of a device 10 for drawing fluid from a lumen according to an embodiment of the present invention. The device 10 comprises a body 11, a first needle portion 12 and a second needle portion (obscured) that is covered by a flexible sheath 13. During transportation and storage the first needle portion 11 is covered by a first needle cap 14 while the second needle portion (obscured) is covered by a second needle cap 15.

The first needle portion 12 is in the form of a tubular puncture needle adapted to puncture a patient's skin (not shown) in order to draw fluid (such as blood) through the device 10.

The device 10 is provided with retaining means 16 in a forward portion of the body 11, the retaining means 16 being adapted to retain the first needle portion 12 in place within the body 11. The rear portion of the body 11 is provided with a screw-threaded portion 17 adapted to facilitate connecting the device 10 to a complementary screw-threaded portion of a medical device (not shown). In use, when the device 10 is brought into communication with a medical device (not shown), the second needle portion (obscured) is held against a seal (such as a membrane, bung, plug or the like) in the medical device and a force is applied to the device 10 such that the second needle portion (obscured) punctures the flexible sheath 13 from within and simultaneously punctures the seal of the medical device. In this way, fluid may be retained within the device 10 until such time as the device 10 is in communication with a medical device (not shown).

The body 11 includes an observation portion 18 fabricated from a transparent or semi-transparent material, and through which the fluid "flash" inside the body 11 may be observed. The observation portion 18 is provided with a plurality of recesses 19 in the form of channels or grooves that are adapted to refract, multiply and/or enhance the image of the fluid within the body 11.

Figure 2:
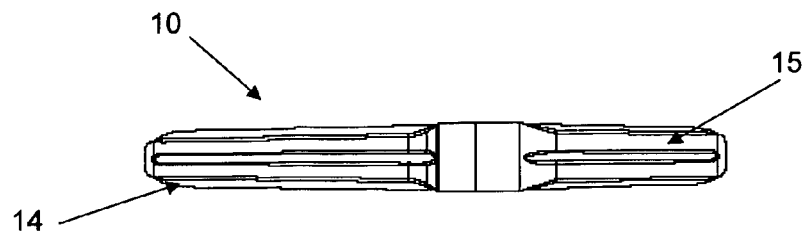
FIG. 2 illustrates a side view of a device for drawing fluid from a lumen according to an embodiment of the present invention.

In FIG. 2 there is shown a side view of a device 10 for drawing fluid from a lumen. In this Figure, the device 10 is shown in its storage or transportation condition, wherein the first and second needle portions (obscured) are covered by the first needle cap 14 and the second needle cap 15 respectively. In this way, the device 10 may be stored and transported without damaging the needle portions and maintaining the sterility of the device 10.

Figure 3:
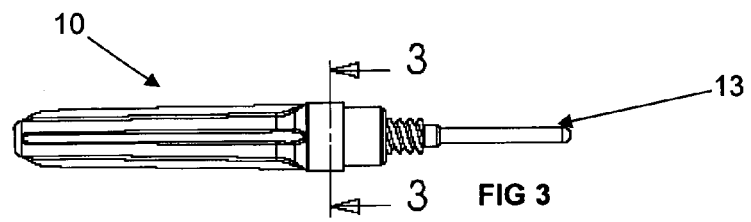
FIG. 3 illustrates a side view of a device for drawing fluid from a lumen according to an embodiment of the present invention.

In FIG. 3 there is shown a side view of a device 10 for drawing fluid from a lumen. In this Figure the second needle cap (not shown) has been removed to expose the flexible sheath 13 covering the second needle portion (obscured).

Figure 4:
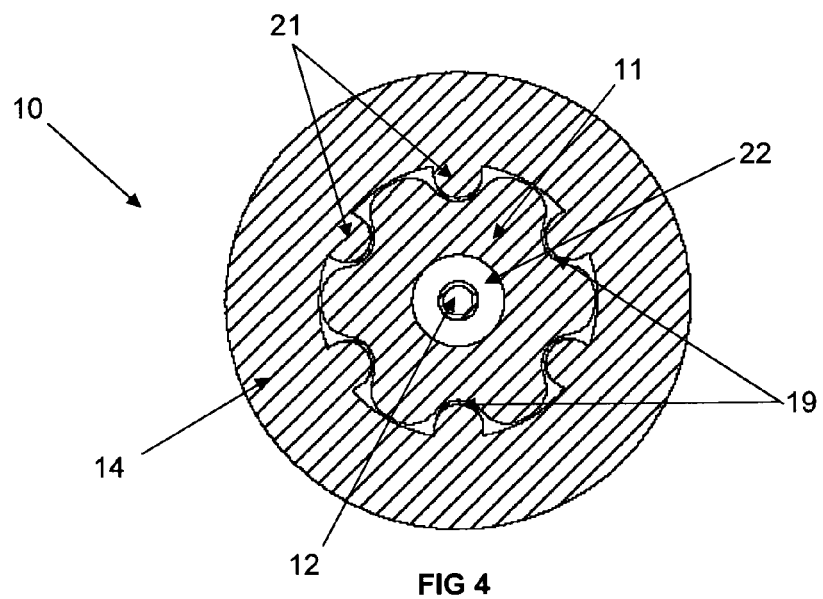
FIG. 4 illustrates a cross-sectional view of the device for drawing fluid from a lumen illustrated in FIG. 3 through section 3-3.

FIG. 4 illustrates a cross-sectional view of the device 10 for drawing fluid from a lumen illustrated in FIG. 3 through section 3-3. In this Figure it may be seen that the first needle cap 14 is provided with a plurality of projections 21 thereon. The projections 21 are adapted to be located in the recesses 19 in the body 11. Preferably, the projections 21 engage with the recesses 19 in a frictional engagement so as to prevent the needle cap 14 from falling off or being knocked off inadvertently during storage or transportation (or the device 10 slipping out of the needle cap 14 when being prepared for use).

In addition, the projections 21 prevent the needle cap 14 from spinning on the device 10 when the device 10 is being connected to a medical device (not shown), for instance in a screw-threaded engagement. Thus, the projections 21 effectively transfer rotational torque to the device 10 so that the device 10 may be securely attached to a medical device (not shown).

In this Figure, it may be seen that the first needle portion 12 extends through the body 11. The first needle portion 12 is substantially tubular such that fluid withdrawn from a lumen passes through the interior of the first needle portion 12. In addition, a chamber portion 22 in the form of an annular ring surrounding the first needle portion 12 (and substantially co-axial therewith) may be seen.

In FIG. 5 a perspective view of a device 10 for drawing fluid from a lumen is shown. In this Figure, the tubular nature of the first needle section 12 may be seen, along with the retaining means 16 in a forward portion of the body 11.

It may also be seen that the recesses 19 in the observation portion 18 extending substantially co-axially with the first needle portion 12. The recesses 19 are substantially concave so that even a small amount of blood flash will be refracted and multiplied so that a user will immediately be aware that the first needle portion 12 is correctly positioned.

Turning now to FIG. 6, there is shown a sectional perspective view of a device 10 for drawing fluid from a lumen. In particular, the rear portion of the device 10 is shown. In this Figure the second needle portion 23 may be seen extending through the rear portion of the device 10. The second needle portion 23 is surrounded by (and substantially co-axial with) the chamber portion 22 along a portion of the length of the second needle portion 23.

The second needle portion 23 is covered along a portion of its length by the flexible sheath 13 that prevents fluid in the second needle portion 23 from being lost or contaminated or from coming into contact with a user. When the second needle portion 23 is brought into contact with a medical device (not shown), the second needle portion 23 simultaneously punctures both the seal (or bung etc) of the medical device (not shown) and the flexible sheath 13, allowing fluid to flow from the second needle portion 23 into the medical device.

In addition, the flexible sheath 13 is resealable, such that, if multiple medical devices (such as blood collection tubes) must be connected to the device 10 in a sequential manner, the sheath 13 will cover the second needle portion 23 once a first medical device is removed and before a second medical device is connected. In this way, the second needle portion 23 is covered to prevent accidental injury or fluid flow through the needle while no medical device is attached.

FIG. 7 illustrates a cross-sectional view of a device 10 for drawing fluid from a lumen. In this Figure it may be seen that the first needle portion 12 and the second needle portion 23 are actually opposing ends of a single needle. The needle is provided with an aperture 24 that is aligned with the chamber portion 22 of the body 11 such that some of the fluid flowing through the needle enters the chamber portion 22 through the aperture 24. The fluid entering the chamber portion 22 may be observed through the observation portion 18 of the body 11. The plurality of recesses 19 in the observation portion 18 ensure that, even if only a small amount of fluid enters the chamber portion 22, the image of the fluid will be multiplied or enhanced such that a user will quickly and easily be able to identify the presence of the fluid. Thus, the user will immediately know that the first needle portion 12 is correctly positioned in the lumen.

The forward end of the body 11 is provided with a retaining means 16 which engages with the body 11 and retains the first needle portion 12 therein.

The rear end of the body comprises a screw-threaded portion 17 for allowing the device 10 to be brought into screw-threaded engagement with a suitable medical device (not shown). The flexible sheath 13 may also be seen engaged with and retained on the rear portion of the body 11.

In FIG. 8 there is shown an exploded perspective view of a device 10 for drawing fluid from a lumen. All of the component parts of the device 10 may be clearly seen in this Figure.

Firstly it may be seen that the first needle portion 12 and the second needle portion 23 comprise opposing ends of a single needle, the needle having an aperture 24 therein through which some of the fluid passing through the needle may exit into the chamber portion (obscured).

The needle passes through and is retained in a body 11, the body 11 having an observation portion 18 fabricated from a transparent or semi-transparent material to allow inspection of the interior of the body 11. The observation portion 18 is provided with a plurality of recesses 19 that enhance, refract and/or multiply the image of the fluid in the chamber portion (obscured) making identification of the fluid (such as a blood flash) fast and easy.

The rear end of the body has a flexible sheath 13 attached thereto, the flexible sheath 13 covering the second needle portion 23 to prevent leakage or contamination of the fluid in the needle, and to prevent the user from coming into contact with the fluid in the needle.

The forward end of the body 11 is provided with a retaining means 16 which engages with the body and retains the first needle portion 12 therein.

Finally, the device 10 is provided with a first needle cap 14 and a second needle cap 15 that protect the first needle portion 12 and the second needle portion 23 respectively from damage and contamination during storage and transportation of the device 10.

It will be understood that the present invention provides a number of important advantages over the prior art. Firstly, the presence of the enhancement means allows a user to quickly and easily determine whether the first needle portion is correctly positioned, making the process of drawing the fluid faster and less uncomfortable for the patient. In addition, the ability to rapidly determine the correct location of the first needle portion reduces the likelihood of injuring the patient due to incorrect positioning.

Furthermore, by providing a single needle, rather than first and second needles as in many prior art devices, the number of parts required to construct the device is reduced, as well as the cost and ease of construction. In addition, providing a single needle rather than two separate needles reduces the likelihood that a needle will come loose and fall out of the device, making the device unusable.

Those skilled in the art will appreciate that the present invention may be susceptible to variations and modifications other than those specifically described. It will be understood that the present invention encompasses all such variations and modifications that fall within its spirit and scope.

The invention claimed is:

1. A device for drawing fluid from a lumen, the device comprising:
   a tubular needle comprising
      a proximal end;
      a distal end;
      a tubular wall extending from the proximal end to the distal end thereby defining a cylindrical cavity extending from the proximal end to the distal end;
      an aperture formed in the tubular wall, wherein the aperture is located between the proximal end and the distal end;
      a first needle portion extending from the aperture to the proximal end;
      a second needle portion extending from the aperture to the distal end;
   wherein the tubular needle extends through a body of unitary construction, the body comprising
      a forward portion and a rear portion, wherein the first needle portion extends from the forward portion of the body and the second needle portion extends from the rear portion of the body;
      an annular chamber disposed concentrically along a portion of the tubular needle, the chamber being defined by an inner surface of an outer wall of the body and encloses the aperture, wherein the cylindrical cavity is in fluid communication with the annular chamber, an internal diameter of the annular chamber being greater than an outer diameter of the tubular needle such that a gap is formed between the tubular needle and an inner wall of the annular chamber for allowing flow of the fluid into the annular chamber; and
      an observation portion formed in the outer wall of the body, the observation portion is structured to allow a visual observation of fluid inside the annular chamber, and
   wherein the observation portion is provided with one or more recesses on an outer surface of the outer wall of the body, the one or more recesses being structured to enhance the visibility of the fluid in the annular chamber, and the one or more recesses are formed integrally with the outer wall of the body of the device.

2. A device according to claim 1 wherein the first needle portion is adapted to function as a puncture needle.

3. A device according to claim 1 wherein the second needle portion is adapted to be brought into communication with a medical device.

4. A device according to claim 3 wherein the second needle portion is provided with a cover adapted to prevent leakage of fluid from the second needle portion before the second needle portion is brought into communication with the medical device.

5. A device according to claim 3 wherein the medical device comprises a fluid collection vessel, flexible tube, or syringe.

6. A device according to claim 1 wherein the fluid is blood.

7. A device according to claim 1 wherein the observation portion is fabricated from a transparent or semi-transparent material and is substantially aligned with the closed, annular chamber such that fluid entering the chamber may be observed through the observation portion.

8. A device according to claim 1 wherein the one or more recesses are angled.

9. A device according to claim 1 wherein the device further comprises a retainer adapted to seal one or more ends of the body and/or to retain the first needle portion and/or second needle portion in place.

10. A device according to claim 9 wherein the retainer comprises one or more retaining caps or retaining plugs.

11. A device according to claim 1 wherein the rear portion of the body is provided with a connector adapted to allow the device to be connected to a medical device.

12. A device according to claim 11 wherein the connector comprises a screw-threaded portion.

13. A device according to claim 1 wherein one or both of the first and second needle portions are provided with needle caps during transportation and storage.

\* \* \* \* \*